US010802032B2

(12) United States Patent
Festoff (10) Patent No.: US 10,802,032 B2
(45) Date of Patent: Oct. 13, 2020

(54) BLOOD DIAGNOSTICS FOR EVALUATING AND PREDICTING BRAIN DAMAGE AFTER A CONCUSSION OR OTHER HEAD INJURY

(71) Applicant: Barry W Festoff, Kansas City, MO (US)

(72) Inventor: Barry W Festoff, Kansas City, MO (US)

( * ) Notice: Subject to any disclaimer, the term of this patent is extended or adjusted under 35 U.S.C. 154(b) by 327 days.

(21) Appl. No.: 14/153,033

(22) Filed: Jan. 11, 2014

(65) Prior Publication Data

US 2019/0293663 A1      Sep. 26, 2019

Related U.S. Application Data

(60) Provisional application No. 61/751,621, filed on Jan. 11, 2013.

(51) Int. Cl.
*G01N 1/00* (2006.01)
*G01N 33/68* (2006.01)

(52) U.S. Cl.
CPC ... *G01N 33/6896* (2013.01); *G01N 2333/988* (2013.01); *G01N 2800/28* (2013.01)

(58) Field of Classification Search
CPC ...................................................... G01N 1/00
See application file for complete search history.

(56) References Cited

U.S. PATENT DOCUMENTS

2014/0110273 A1* 4/2014 Bar-Or ............... G01N 27/4168
205/792

* cited by examiner

*Primary Examiner* — Jyoti Nagpaul
(74) *Attorney, Agent, or Firm* — Sandberg Phoenix & von Gontard P.C.

(57) ABSTRACT

Methods and materials are disclosed for evaluating head brain injuries that do not involve blood loss or skull fractures, such as possible concussions. These methods and materials involve bioreagents (such as monoclonal antibodies, single-stranded DNA or RNA, etc.) affixed to computer-readable devices handled by electronic readers that can interact with portable computers (such as laptops, pads or tablets, smart phones, etc.). The bioreagents will detect the presence and concentration of at least two metabolites that are released by mitochondria in response to cellular damage. Additional bioreagents may be included, for detecting and quantifying other damage-associated molecular patterns (DAMP's). When used along with cognitive, reasoning, and/or response tests, this type of analysis can help non-physicians assess the severity of, and proper responses to, head traumas that otherwise are difficult or impossible to reliably evaluate.

4 Claims, 1 Drawing Sheet

BLOOD DIAGNOSTICS FOR EVALUATING AND PREDICTING BRAIN DAMAGE AFTER A CONCUSSION OR OTHER HEAD INJURY

RELATED APPLICATION

This application claims priority under 35 USC 119 based on provisional application 61/751,621, filed on Jan. 11, 2013.

BACKGROUND OF THE INVENTION

This invention is in the field of neurology and medical technology, and relates to diagnostic methods for evaluating the severity of a concussion or comparable type of head trauma.

Within the medical profession, injuries to the head and/or brain which are caused by forceful impacts are classified as "mild" (even though some such injuries may lead to serious and even severe long-term damage), if certain types of indicators are not present which would otherwise indicate a need for immediate hospitalization and critical-care intervention.

According to the U.S. Center for Disease Control (CDC), mild traumatic brain injury (TBI), which stops short of a concussion, likely affects between 1.5 and 2 million people annually, in the US. The CDC also estimates between 3.5 and 4 million people annually suffer from the types of more severe head injuries that probably should be classified as concussions. They further estimate that 15 to 20% of this number will go onto post-concussion syndrome (PCS), usually within 7 to 10 days after the concussion; about 50% of those individuals will continue to suffer from symptoms of PCS, three months after the head trauma, and 20% will still have symptoms a full year after the injury.

Trained specialists who work in hospital admitting rooms use an evaluation system which assigns a "Glasgow Coma Score" (GCS) to arriving patients. However, those types of evaluations, by trained experts, are reached only after a patient has been taken to a hospital. Accordingly, a major need has arisen for better methods that will allow police, firemen, athletic coaches and trainers, ambulance attendants, and other semi-trained laypersons to accurately and reliably evaluate what appears to be a "mild" head injury, at the site where an accident or other similar even occurred.

As a classic example, in the sport of football, players are often momentarily stunned by hard or severe tackles. That is an integral part of the game, and it is referred to by vernacular phrases such as, "He got his bell rung." In most such instances, using common practices, the player is told to sit on the bench for a play or two, and then "walk it off," if he can do so. He is visually monitored, and asked some questions, such as, "Do you know what day it is? Where are we? Who are we playing against?"

If a person who has suffered a head injury:

(i) give signs of having suffered a broken bone;

(ii) has blood emerging from an eye, ear, nose, or similar site;

(iii) suffers a loss of consciousness lasting longer than half a minute or so; or, (iv) fails to answer simple questions, fails to talk coherently, or gives other signs that a major disruption of normal neurologic functioning is occurring, then the head injury is classified as moderate or severe, and appropriate action is taken, such as calling an ambulance, taking an athlete into a locker room for further evaluation, etc.

However, if the victim of a head injury does not suffer from those types of indicators, and can answer questions and walk and then run without assistance, the trauma usually will be presumed to be "mild", and the coach (and any trainer(s) who may be present, at a collegiate or professional event) will have to reach a "best guess" appraisal of whether the athlete can safely return to the game.

For anyone who has not competed in sports at a collegiate or professional level, and who has not dedicated a huge portion of their life (including countless hours of practice and workout time) to a game, it can be difficult or even impossible to understand the power and urgency of the motivation that will drive coaches and athletes to risk long-term brain damage, in a truly talented, promising, and hopeful young person, for the sake of simply re-entering a game. That motivation is directly akin to the "bonding" that great soldiers feel for their "brothers in arms", to a point where a soldier will literally sacrifice his life for his "brothers". In sports, and especially in football, the prevailing ethos can be summarized best by an immortalized phrase attributed to Vince Lombardi, regarded as one of the greatest football coaches who ever lived: "Winning isn't everything. It's the ONLY thing." If a seemingly distant and unlikely prospect of some sort of unknowable long-term problem must be balanced against an immediate and pressing threat of losing a crucially important game, at a collegiate or professional level, where the lives, happiness, future careers, and incomes of everyone on the team have been put on the line on a win-or-lose basis, then the immediacy of the competition, and the excitement and pressure of the game, tend to loom quite a bit larger than a small risk that can't be pinned down, can't be proven, and probably will never happen. Without exaggeration, that is the type of thinking and attitude that has prevailed among most top-level, hyper-competitive collegiate and professional football teams, for decades.

Diagnosis of either concussion, or its somewhat lesser cousin, mild TBI (mTBI), is poor and inaccurate, and even at best, diagnosis of borderline cases (which are very frequent) is heavily subjective as described below. Over the last decade and a half, intensive efforts towards defining objective and clinically-useful biomarkers have not been successful, in large part because the blood-brain barrier (BBB) is very efficient at keeping most types of extracellular molecules either inside the brain, or outside the brain. The BBB not only serves to prevent blood-borne molecules from entering brain tissue, where they would contact neurons directly; it also limits the passage of most large molecules from the brain, to the blood circulation. This has a considerable impact on clinical efforts to diagnose concussion and/or mTBI, since accuracy of diagnosis is essential for successful management.

However, things are changing. Beginning in about 2010, a series of widely-reported suicides occurred, among former professional football players who were suffering from severe long-term mental problems. Indeed, several retired football players shot themselves through the heart, while leaving behind suicide notes which explicitly asked that their brains be preserved, and examined, to help improve our medical understanding of long-term brain damage caused by repeated concussions).

In 2011 and early 2012, more than 75 lawsuits were filed against the National Football League (NFL), by or in behalf of former players, with essentially all of them alleging that the NFL knowingly withheld or ignored information on the long-term seriousness of concussions. In June 2012, those lawsuits were consolidated into a class-action lawsuit (the largest sports-related lawsuit ever in history, in any sport) in behalf of hundreds of former professional football players, seeking literally billions of dollars in damages from the owners of the National Football League. In August 2012, the NFL agreed to pay $765 million into a fund to settle those lawsuits, and to compensate and provide better care for players who suffered concussions or other brain injuries during their playing careers.

In addition, anyone who is seriously interested in this subject should be aware of various "expose"-type articles, television shows, and books, which make concerted efforts to portray the actions of NFL owners, boxing promoters, and others, as actively malevolent. Since this application is not intended to take sides on anything other than a true and pressing need for better diagnostic methods, those are not listed herein, but can be found by anyone who looks for them diligently.

Finally, those who are interested in this subject should also be aware of various studies into a condition called punch drunk syndrome, also called dementia pugilistica and/or chronic traumatic encephalopathy (CTE).

Accordingly, it would be highly useful if coaches and trainers, on collegiate and professional sports teams (and at any other level, such as high school, junior high school, and even Pew Wee and Pop Warner leagues), and in any sport which poses a risk of serious collisions or violent impacts, could have and use a simple and convenient diagnostic tool or method, which could provide a valid and reliable indicator of whether an athlete who has been stunned or shaken up (i.e., briefly rendered unconscious, disoriented, or similarly affected), by a collision or similar impact, can safely return to a game after a few minutes of settling down, or whether that athlete needs either:

(i) a longer period of rest and recovery, in a dark and quiet room that can enable the nervous system to reestablish equilibrium and "homeostasis"; or, (ii) other medical attention, possibly including on-site medication, such as pain-killers and/or sedatives that can help control the disruptions and challenges that a player's nervous system is struggling to withstand and recover from, which in some cases should be administered immediately while steps are also commenced to transport the injured person as quickly as possible to an emergency room or clinic.

Beyond those types of sports-related injuries, numerous other types of trained personnel (including police, firemen, ambulance attendants, and even teachers and various types of caregivers) encounter situations where they witness (or are called upon as a "first-responder" to) an accident which may involve a concussion or similar mild TBI, and which raises questions about the best form of treatment for the victim. Although the general rubric of "playing it cautious" (i.e., by having any victim of an apparent head trauma lay down and rest quietly) is generally applicable, numerous questions can arise, including:

(i) whether emergency medical care, beyond merely laying down quietly, should be obtained; and, (ii) whether the person's feet and legs should or should not be elevated, to increase blood flow to the torso and head.

Furthermore, since more than one victim is involved in many accidents, "first-responders" such as police, firemen, and ambulance attendants must often reach a rapid decision as to which victim(s) will be treated with urgent priority, while others will need to wait until after one or more critically injured victims have been treated or taken away. When these types of problems arise, head traumas that may appear to be mild, leading to little more than apparently brief and transient disorientation, can pose extremely difficult and vexing problems, since the brain is an extraordinarily fragile and vulnerable organ, which in some instances can temporarily mask the extent of damage that was caused by an accident, while the damage continues to increase and grow much worse, inside the skull.

Prior Art Re: Diagnosing Concussions and Similar Head Traumas

There are several recent published patent applications that describe various proposed approaches to evaluating the severity of a head trauma that may have risen to the level of a concussion. They clearly are designed primarily, or at least initially, for use at locations such as on the sidelines of a professional or possibly collegiate football game, although they mention that such methods and devices can also be used elsewhere.

One such device, described in published US patent application 20020011250 (Stewart), relates to a mobile, hand-held electronic device that is used to record and analyze various data points, as a football player who was shaken up by a hard hit (or any similar person) is asked questions and requested to perform certain physical tasks.

A somewhat more complex device, described in published application 2008-0208073 (Causevic), would require that a player be given an "electroencephalograph" (EEG) test. That presumably should be done in a locker room, to eliminate the risk that the sound of the crowds and the views of the game might affect the results, but it can be performed on the sidelines, if desired, using a moderately small array of electrodes, and an electronic device which presumably would be roughly the size of a conventional desktop printer.

A substantially more complex approach, which would require a shaken-up player be taken to a locker room, is described in US application 2012-0083688 (Nauman et al). It would utilize medical-type brain imaging, using methods such as "functional magnetic resonance imaging" (usually abbreviated as fMRI), to obtain actual live images of how the brain tissue is responding to the "blow to the head".

Any or all of those three approaches might well be useful, and almost certainly could offer an improvement over the diagnostic level that is reached when a trainer merely asks a shaken up player, "What day is it? And how many fingers am I holding up?"

However, in the view of the Applicant herein, none of those types of evaluative methods (not even the use of a sophisticated tissue-imaging machine) will be sufficient to provide a complete and reliable evaluation, because of the complicated interactions between a number of cellular, biochemical, and neurological factors, described below. Briefly, any of the evaluative devices and methods listed above can create what is, by way of analogy, a "snapshot" that is limited to the moment when it was taken. Just as a snapshot cannot predict the future (except in a few rare instances that are not of interest herein, such as a snapshot of an out-of-control plane or speeding car that is only moments away from crashing), neither can the types of diagnostic tools that are provided by the types of devices described in the patent applications listed above.

Instead, a truly adequate system for diagnosing the true severity of (and the future risks created by) a blow to the head, needs to be able to predict what will happen, over the course of the next few hours.

Accordingly, a genuine grasp and understanding of THAT type of challenge, and that level of difficulty, requires a three-part digression into a set of medical and neurological facts, factors, and risks that arise, when one begins to wrestle with the question of, "Just how severe, and how dangerous, was that blow to the head?"

Three Factors that can Aggravate and Multiply Delayed Brain Damage Over a Span of Hours There are a number of biochemical and neurologic factors which can cause or aggravate brain damage, and even death, over a prolonged span of time (typically measured in hours, rather than minutes), following an "extra-hard tackle" or other blow to the head. Three such factors, in particular, are sufficiently important, and common, to merit attention, by anyone who is truly interested in this subject and who wants a better understanding of how head injuries can lead to permanent brain damage, or even death.

Factor 1: Neuronal Membranes, Voltages, and Ion Pumps

The FIRST major factor that needs to understood, by anyone studying this line of medical science and terminology, involves neuronal membranes, membrane voltages created by charged ions, and ion pumps. These neuronal components, activities, and principles are well-known, and are described in any good textbook on physiology or neurology.

In vertebrate animals, there are only two main types of excitatory neurotransmitters. They are called glutamate (i.e., the stable ionized form of an acid called glutamic acid), and acetylcholine (abbreviated as ACh). The other major neurotransmitters (including dopamine, serotonin, and GABA) are all inhibitory, and they are used to modulate and control the effects of the two excitatory transmitters, glutamate and ACh.

When a molecule of either glutamate or ACh is released into the watery fluid that fills the "synaptic junction" between a signal-transmitting neuron, and a signal-receiving neuron, the excitatory neurotransmitter molecule will bind, for a brief instant (measured in milliseconds), to a receptor protein that is embedded within the "synaptic membrane" of the signal-receiving neuron.

As a brief digression to explain an important term, for anyone who is not yet an expert in this field but who wants to make a diligent effort to learn more about how how neurons behave and why they are so highly susceptible to damage, the terms "synapse" and "synaptic" refer to the junctions, between neurons, where signals are transmitted. Because of how they are structured, each synapse provides a one-way interface, where a signal-transmitting neuron will release one or more specific types of neurotransmitter molecules into a small gap that is filled with a watery fluid. The neurotransmitter molecules that are released at any particular synapse will be limited to only only type of neurotransmitter, and different synapses use glutamate, ACh, dopamine, serotonion, GABA, or any of several other less-common neurotransmitters. At an active synapse, a neurotransmitter molecule released by a signal-transmitting cell will briefly contact and bind to the exposed portion of a "signal receptor", which is a small structure created by several protein molecules (usually called subunits) that fit together in a specific pattern.

When either of the two excitatory neurotransmitters (i.e., glutamate or ACh, as mentioned above) are involved, a binding reaction between the released neurotransmitter molecule, and the synaptic receptor, causes the nerve-signal receptor to undergo a change which triggers the opening of one or more ion channels, which pass through the outer membrane of the receptor neuron. The opening of an ion channel allows charged ions (including chlorine (Cl−), sodium (Na+), and potassium (K+), which crowd up against the internal and external surfaces of the cell membrane) to go rushing through the ion channel, during the brief instant while the channel is open. That brief flow of ions, through an open ion channel, will cause the "voltage potential" across the cell membrane, to drop from a "resting state" (about 90 millivolts), to a "depolarized" state (usually with a voltage of about 65 millivolts). That drop in voltage (often called a depolarization, firing, or nerve-firing event) is the biochemical event which is interpreted as an arriving nerve signal, by the signal-receiving neuron.

A rapid drop in voltage, across a neuron's outer membrane (caused by receptor-activated opening of an ion channel), will activate a sequence of responses by the neuron, which include:

(1) release of its own neurotransmitter molecules, at other synaptic junctions (often called "downstream" synapses) which the signal-receiving neuron shares with other neurons;

(2) closure of the ion channels, to prevent further reduction in the voltage gradient across the outer membrane of the signal-activated neuron; and, (3) turning on a set of ion pumps, which the receptor neuron will then use to pump the charged ions into and out of the cell again, so that the neuron can regain its "resting state" voltage of 90 millivolts.

The "resting state" voltage gradient, across a neuron's outer membrane (which is about 90 millivolts, for most types of neurons), is absolutely crucial to any neuron, since it allows the neurons in any type of higher animal to respond very rapidly, whenever a new nerve signal arrives. Otherwise, a signal-receiving neuron would first need to carry out some type of preparation process, after a nerve impulse arrived, before the neuron could respond to the incoming nerve impulse. Those types of delays would render it impossible for animals to respond quickly to signals that indicate food, danger, etc. As a result, over the course of evolution, nervous systems evolved which allow higher animals to respond immediately to outside stimulus. That arrangement requires neurons to perform a lot of work, in advance, to get ready to "fire", immediately, as soon as a new nerve impulse arrives. This is reflected in the fact that the "resting state", for any neuron, is actually a high-energy state (which can be referred by phrases such as "fully-loaded, primed, cocked, and ready to fire"). As mentioned above, the resting state for a neuron requires a "voltage gradient" of about 90 millivolts (nearly 1/10th of a volt), across an extraordinarily thin membrane which is far too small to see with a naked eye. That "voltage gradient" is created by ion pumps, and the ion pumps in the brain and spinal cord use up and consume roughly 1/5 of all the food-derived chemical energy that is being consumed by the entire body of a human, at any given moment.

If neurons in the brain or spinal cord are prevented, by some type of injury or other insult (such as a loss of its blood, oxygen, or fuel supply) from being able to use their ion pumps to pump enough ions into and out of their cell bodies to reach their 90 millivolt "resting state", the affected neurons will quite literally kill themselves, through exhaustion and depletion of crucial resources, within a very short span of time. As a simple illustration, if a human brain is deprived of oxygen or blood flow for only about 6 minutes, the neurons will suffer such massive damage that the person will either die, or be condemned to a "permanent vegetative state" for the remainder of his or her "life". This arises directly from the fact that neurons are unavoidably and unchangeably designed, programmed, and committed to turning on their ion pumps, and keeping those pumps turned on, until the pumping activity has lifted and carried the neurons up to a high-energy, "ready to fire" state. Neurons simply cannot shift into a dormant, passive, or quiescent state, to conserve energy if a crisis such as a stroke, cardiac arrest, or loss of oxygen cuts off their energy supply; and, it also should be noted that the brain and spinal cord contain no fat, or any other type of backup, emergency-only, or other "reserve supplies" of stored materials that can be converted into energy, in a time of crisis. Instead, neurons in the brain and spinal cord will quite literally kill themselves, through exhaustion and depletion, if their ion pumps are not able to pump enough ions into and out of their cell bodies to enable the neurons to reach their high-energy "resting state".

Factor 2: Uncontrolled "Free" Glutamate, and Excitotoxicity

The SECOND major factor which merits attention, by anyone who wants to understand the type of brain damage that can be caused by concussions, involves a process that neurologists call excitotoxicity. It is driven by excess accumulation of glutamate molecules, in the watery fluids that fill the gaps between neurons, in synaptic junctions that convey nerve signals between neurons.

As mentioned above, after a molecule of glutamate binds to a synaptic receptor as part of a signal-transmitting event, the glutamate molecule is released by the receptor, and it floats back into the watery fluid that fills the gap, in the synaptic junction between the transmitting and receiving neurons. Any molecules of "free" glutamate (i.e., extracellular glutamate molecules which have been released by a neuron, and which have contacted a receptor, and which have been released back into the synaptic fluid, by a synaptic receptor protein) must be removed from the synaptic fluid, very rapidly, to prevent those glutamate molecules from contacting and binding to other neuronal receptors. If "free" glutamate is not cleared, very rapidly, from the synaptic fluids, it can trigger uncontrolled and unwanted neuronal "firing" events, which would effectively become distracting and harmful "noise" (or static, or similar terms), which could otherwise severely disrupt the normal patterns of nerve signals that are interpreted as perceptions, thoughts, memories, etc.

The brain uses a specialized pumping system, usually called the glutamate transport (or clearing, or pumping) system, to handle the task of removing (i.e., clearing away) free glutamate molecules, from synaptic fluids. This glutamate transport system uses specialized proteins, which are embedded within the outer membranes of neurons and glial cells.

As a side note to briefly explain another crucial term, glial cells include cells (other than cells that help form blood vessels or membranes) that are located within brain or spinal tissue, but are not neurons (i.e., which do not and cannot send or receive nerve impulses). By definition, a "neuron" must be able to send and receive the types of nerve signals that act very rapidly (i.e., measured in milliseconds). Those types of extremely fast cellular responses require specialized synapses and neurotransmitters, rather than the types of much slower surface receptors that are activated by other molecules, such as hormones. Within the brain and spinal cord, there are about six major types of cells that do not contain synapses, and that cannot send or receive nerve signals. The researchers who first identified those cells, after microscopes were invented, did not know what those cells did, so they assumed that those cells held the brain and spinal cord together, and they called them "glial" cells, derived from the same root word as "glue". As the study of neurology gradually improved, it became clear that glial cells are not merely tissue-cohesion cells; instead, there are different types of glial cells, and each type performs support functions that are crucial for nurturing and protecting neurons, in ways that allow the neurons to handle, interpret, and generate nerve signals in extraordinarily rapid ways. Accordingly, the term "glial cells" now refers to and includes any cells, in the brain or spinal cord, that do not send or receive nerve signals, and that are not part of blood vessels or membranes.

Returning to the "glutamate transport system", there are large numbers of specialized cell-surface proteins, called "glutamate transport proteins", on the surfaces of both neurons and glial cells. Those proteins will "grab" any molecules of "free" (extracellular) glutamate that are present in the watery "cerebrospinal fluid" (abbreviated as CSF), and pump those "free" glutamate molecules back into the interiors of the neurons and glial cells. The large majority of free glutamate is grabbed by neurons, which will re-use the glutamate in subsequent nerve-signal transmissions. The remaining trickle of free glutamate is taken up by glial cells, which gradually accumulate substantial quantities of glutamate in their interiors.

Glial cells use glutamate mainly as a building block for making proteins, since glutamate is actually one of the 20 "primary" amino acids that are used to synthesize proteins. It is a curious accident of evolution that higher animals actually use the same molecule, glutamate, as both a building block for all proteins, and as a neurotransmitter. Those two usages are directly contradictory; the first usage requires glutamate to be present and available, in substantial quantities, in all living cells, so that the cells can make new proteins as needed; however, the second usage require a specialized and tightly-controlled handling system, within brain and spinal cord tissue, to prevent that same widely-distributed molecule from causing major problems by triggering unwanted and distracting nerve signals.

Importantly, it requires fuel, and energy consumption, to drive and run the glutamate transport system (i.e., the protein pumps on the surfaces of neurons and glial cells, which grab any free glutamate molecules and pump them into the interiors of the cells). Therefore, if the supply of energy to drive the glutamate transport system is damaged or disrupted in all or some portion of the brain (such as by a stroke, severe blood loss, cardiac arrest, or other medical crisis), the glutamate transport system will begin to fail, and free (i.e., extra-cellular) glutamate will begin to accumulate in the fluids that fill the synaptic junctions between neurons.

If that begins to happen, within the brain of someone who has suffered an apparently "mild" brain trauma (i.e., who is not bleeding from the skull, or babbling incoherently, but who was "banged on the head" with a level of severity that cannot be evaluated quickly or reliably), then any "free" glutamate molecules can rapidly become extremely serious and even deadly trouble-makers. The same neurotransmitter molecules which are essential to nerve signal transmission, during normal and healthy conditions, will become toxic and even deadly, if something disrupts (or even just impairs and reduces) the rate (or the evenly-distributed allocation) of blood flow through the brain.

This occurs because, in an area of the brain where blood flow is disrupted, thereby depriving that brain tissue of the fuel and energy it needs to run the glutamate transport system, "free" glutamate molecules will begin "hammering" at glutamate receptors, in multiple synaptic junctions within an energy-deprived portion of a brain, in an uncontrollable manner. Each time a free, uncleared glutamate molecules bumps into a glutamate receptor, in a synapse within an energy-starved part of a brain that is suffering a crisis, it will trigger a receptor response. The affected neuron will open that receptor's ion channel, which will lead to a rush of charged ions in both directions through the open channel. That channel-opening event will "depolarize" and "fire" that neuron, causing its membrane voltage to drop down below the 90 millivolt "resting state".

The affected neuron will then respond by: (1) releasing its own neurotransmitter molecules, usually at multiple "downstream" synapses, which can cause other, additional neurons to be dragged into the expanding and worsening crisis; (2) closing its own ion channel, and (3) turning on its ion pumps, in an effort to try to regain its 90 millivolt "resting state", so that it will be ready to receive the next nerve signal.

It requires (and consumes) a great deal of energy, to drive the ion pumps that enable neurons to function properly, in any higher animal's brain and spinal cord. In humans, even though the brain and spinal cord weigh only a few pounds, they consume a fifth of all the oxygen that is carried by blood. A very large portion of the energy that is released, when oxygen is used to effectively "burn" (i.e., oxidize) glucose (an energy-rich form of sugar), to break down the energy-rich large molecules into carbon dioxide and water, is used to drive the ion pumps, which are absolutely crucial to the neurons.

Therefore, if the neuronal ion pumps begin to be repeatedly "hammered" in an uncontrolled manner, by "free" glutamate in a part of the brain where blood flow or oxygen supply has been lost or reduced due to a stroke or other medical crisis, the affected part of the brain can rapidly be driven into a toxic "cascade", where neurons will begin dying, in large numbers, due to exhaustion and depletion.

Furthermore, when the glutamate receptors on the synaptic surfaces of neurons in a directly-affected portion of the brain begin to be "hammered" uncontrollably by uncleared glutamate, the affected neurons will begin releasing uncontrolled quantities of their own neurotransmitters, at additional "downstream" synapses. This will cause the directly affected neurons to pull and drag other, additional neurons, elsewhere in the brain, into the toxic cascade. This type of damage has been recognized for decades, based on studies of "localized" strokes (often called "focal" strokes or ischemia, as compared to a "global" stroke or ischemia which will affect the entire brain, as caused by a crisis such as complete cardiac arrest, or severe blood loss). Limited and localized ("focal") strokes usually occur when a clump of fat or bacterial growth, or a blood clot, detaches from wherever it formed, inside a blood vein somewhere in the body, and travels through the blood vessels until the clump or clot reaches a juncture in the brain where an artery divides into smaller arteries that are too small to allow the clump or clot to continue traveling. When that type of obstruction cuts off blood circulation through a limited portion of the brain (i.e., the brain tissue which was serviced by the artery that became blocked), it usually causes both: (1) rapid death and necrosis, in the region that was directly deprived of blood flow; and, (2) an additional area of damage, where some but not all of the neurons will be killed. That type of additional damage is often referred as "penumbral" damage.

When a stroke victim is put into a "controlled coma", using powerful sedative drugs, the main goal is to minimize the area and the extent of the additional "penumbral" damage within the brain (i.e., the damage in areas that were not doomed by a direct loss of their blood supply). This type of treatment is a direct response to the process called "excitotoxicity", in which: (1) the "glutamate transport system" fails, in a limited portion of the brain, because its energy supply is temporarily cut off; and, (2) the "free" (i.e., "uncleared", extra-cellular) glutamate begins to create a "vicious cycle" type of damage, which initially arises only in a limited region, but which then begins to "feed itself", and expand aggressively into other parts of the brain, in ways that can severely damage other, additional parts of the brain.

The process called "excitotoxicity" poses one of the largest and most intractable problems and challenges, to physicians who try to minimize the extent and severity of brain damage, in victims of stroke, severe head traumas, cardiac arrest, and other types of medical crises that affect the brain. Accordingly, that process needs to be recognized, and understood, as a hugely and crucially important and dangerous risk factor, in any event that might initially appear to be a "mild" head trauma. Even if the trauma itself only appears to stun or disorient the victim for a few minutes, it poses a risk of triggering a toxic cascade of permanent excitotoxic damage inside the brain, which will play out and become apparent only over a span of hours, or days, rather than minutes.

For completion, it should also be mentioned briefly that the other main excitatory neurotransmitter, ACh, does not pose any similar risk of excitotoxic damage, after a head trauma. After an ACh molecule reacts with a synaptic receptor and is released by that receptor, the "free" (extra-cellular) ACh will be grabbed and processed by an enzyme called cholinesterase, which will break apart the ACh into two components which cannot trigger more nerve-signal firing events. Those two "building blocks" of ACh will eventually be grabbed by transport proteins, and pumped back inside neurons, so that enzymes in the neurons can reassemble those building blocks into new ACh, which can then be used in subsequent nerve-firing events. The reaction in which an ACh molecule is split apart, by a cholinesterase enzyme, is an exo-thermic reaction, i.e., an energy-releasing reaction. Since it releases energy, rather than requiring and consuming energy, that reaction will continue to inactivate "free" ACh, even during a major crisis such as a stroke or severe head trauma.

Accordingly, the process called "excitotoxicity" is initially created and driven entirely by glutamate, rather than acetylcholine.

Nevertheless, the role of acetylcholine, in creating and inflicting excitotoxic damage within an injured brain, cannot be ignored, since ACh neurotransmitter molecules will be released at "downstream" synapses, by neurons that are having their "upstream" receptors "hammered" by abnormal quantities of free glutamate, in a crisis situation. When surplus ACh molecules are released inappropriately, by neurons that are being "hammered" by unwanted and neurotoxic free glutamate, the ACh molecules will help to severely aggravate and increase the brain damage that will result, because they end up driving still more affected neurons into an aggravated crisis condition. Every over-excited neuron, regardless of whether it was triggered by glutamate or ACh, will begin scrambling, and competing against other neurons, to obtain as much as possible of the dwindling supplies of glucose and oxygen, which provide the fuel which enables neurons run their ion pumps.

Factor 3: Elevated Fluid Pressures, Inside the Skull

The third major factor which requires attention, by anyone who seeks to understand the types of brain damage that can be caused by a concussion or other head trauma, is often referred to, in layman's terms, as "swelling of the brain". Since the brain, which is trapped inside the hard encasement provided by the skull, cannot actually "swell" except in limited ways (such as by causing the eyes to "bulge out"), the true problem is usually referred to in medical terms as elevated levels of "intracranial pressure" (which can be abbreviated as either IP, or ICP).

Because of certain factors and processes that do not require attention at this time, brain cells and brain tissues can and will swell up, when they are injured, in a manner that is comparable to the way a hand, wrist, foot, or ankle will swell up, if it is hit hard by a hammer or any other hard object, or if it becomes infected by pathogenic microbes. Terms such as "inflamed" and "engorged" are often used, to describe what happens when soft tissue that has been injured or infected swells up and becomes painful; the medical term "edema" is also used, to refer to any unusual, unwanted, and/or harmful accumulation of liquid (usually blood and/or lymph), within a limb, extremity, organ, or other soft tissue.

Critically important differences arise, in terms of what will happen to a brain (as compared to a hand or foot), if the levels of intracranial pressure (ICP) rise up above normal levels. Rather than causing the brain to actually swell up (which cannot happen to any significant level, so long as the skull remains closed), increased fluid pressures inside the skull will begin pressing against the walls of the capillaries inside the brain. Capillary walls are extremely thin, to enable rapid and efficient transfer of oxygen and nutrients out of circulating blood and into surrounding tissues, and to enable waste metabolites to be quickly transferred into the blood, from the tissues. As a result, the capillaries inside the brain can be squeezed shut, by the levels of elevated pressures that can arise inside the brain after a head trauma. Because of basic and unavoidable fluid mechanics, even a relatively slight and modest increase in fluid pressures, inside the skull, can cause blood to stop flowing through the brain. Arterial blood, pressurized by the beating of the heart, will simply flow through other blood vessels that are not in the brain, where pressures and resistance are lower.

Any cutoff or serious reduction, in blood flow through the brain, can rapidly cause a loss of consciousness, and it will result in death, if not treated within a few minutes. Accordingly, emergency steps must be taken to treat any patient in that condition. In the field, the victim's legs should be raised, and the head should be lowered as much as possible, to use fluid mechanics and hydrostatic pressure to try to reestablish blood flow through the brain. When an ambulance arrives, the ambulance attendants will often place specialized pants (often called "MAST" pants, which refers to "military anti-shock trousers", initially developed for pilots of fighter planes) on the patient; when specialized tubing embedded within the legs of those pants is inflated, the pants will tighten, and constrict the legs, in a manner which effectively drives blood out of the legs and promotes more blood flow through the brain. In addition, the ambulance attendants may begin administering stimulant drugs (comparable to adrenalin) to a patient, to temporarily boost the strength of the heartbeat, in an effort to restore circulation through the brain.

When a patient suffering from brain swelling reaches a hospital, and will not respond adequately to other prior treatments, surgeons will often use specialized drills and saws to remove a portion of the skull from the patent's head, to create a "window" that will allow the swelling brain to physically protrude out beyond its normal skull-encased volume, for a few days, while potent drugs and other measures are used to bring the swelling under control. There are thousands of people who are alive today, who had a portion of their skull removed for several days, to open up a "window" that would help them survive an episode of severe brain swelling, after near-fatal automobile accidents, drownings, and other major traumas. In most such cases, the bone segment that was removed from the skull will be preserved, often by using techniques such as temporarily implanting it into the same patient's abdomen, where it will be protected and given a blood supply until the brain swelling has receded. After the brain swelling recedes and intracranial pressures return to normal levels, a followup operation is performed, to retrieve the skull segment from the abdomen, and replace it in its original position, in the skull.

That type of operation—removing a portion of the skull, for several days—is a fair and valid indicator of the fact that tissue swelling, and elevated fluid pressures inside the brain, can shut off or impede blood flow through the brain, at levels which can rapidly cause severe and permanent brain damage, and in many cases will kill the victim, if not treated immediately. The devastating effects of elevated fluid pressure inside the brain are critical, and can rapidly become lethal.

One of the major problems that arises, when a head injury occurs that appears to be mild or moderate, is that under the current state of the art, it is often impossible to know or predict, during the first few hours after the trauma has occurred, whether some particular fall, collision, or other "blow to the head" will actually lead to swelling of the brain, and increased ICP levels, and which ones will not. Stated in other terms, under the current state of the art, it can be difficult or impossible for even trained observers (including, for example, fully-qualified practicing physicians who work as "trainers", on the sidelines, during professional football or hockey games) to know and determine, after a collision or other head trauma has caused temporary stunning or disorientation, whether the stunned person can safely take simple measures to recover (such as sitting or lying quietly for a while, then walking around gently and cautiously for a while, before returning to more active or even strenuous physical activity), and which victims may be teetering on the edge of major and even devastating brain damage, and who should be rushed to a hospital as quickly as possible.

A useful example is provided by the actress Natasha Richardson, who was killed in March 2009 by what initially appeared to be a fairly mild head trauma, which occurred while she was skiing. The following is a brief account (from her Wikipedia entry) of what happened to her, and the progression of stages she went through, during the two days following that accident. It was not a bizarre or "freakish" accident, and the progression of steps that followed, after the accident, was not unusual. Instead, this example is fairly typical of what happens thousands of times, every year:

On 16 Mar. 2009, Richardson sustained a head injury when she fell while taking a beginner skiing lesson . . . . The injury was followed by a lucid interval, when Richardson seemed to be fine and was able to talk and act normally. Paramedics and an ambulance which initially responded to the accident were told they were not needed and left. Refusing medical attention twice, she returned to her hotel room and about three hours later was taken to a local hospital . . . after complaining of a headache. She was transferred from there by ambulance to . . . Montreal, in critical condition and was admitted about seven hours after the fall . . . she died on 18 March at the age of 45. An autopsy . . . revealed the cause of death was an "epidural hematoma due to blunt impact to the head", and her death was ruled an accident.

The medical phrase, "epidural hematoma", refers to bleeding inside the skull, on the outside of a membrane called the dura, which surrounds and normally protects the brain. That type of bleeding, inside the skull, is one type of event that will lead to elevated intracranial pressure, i.e., a trapped and enclosed condition of elevated fluid pressure, which will reduce or cut off blood circulation through the brain. That problem often and typically manifests, initially, as a severe headache. By the time a headache arises and becomes severe, the damage process is well underway, and the headache is usually followed fairly rapidly by convulsions and seizures, which can lead to death unless emergency action is taken.

Finally, it should also be noted that if elevated intracranial pressures begin to occur inside the skull, then the resulting reduction of blood flow through the brain will rapidly begin triggering an uncontrolled release and accumulation of "free" (extra-cellular) glutamate within the brain. That secondary effect arises directly from the factors and effects described in the prior section, under the subheading, "Factor 2: Uncontrolled 'Free' Glutamate, and Excitotoxicity".

Indeed, in a curious and apparently perverse turn of events, glial cells also begin releasing and "dumping" their own stored loads of glutamate, into the extracellular fluids inside the brain and spinal cord, when a major crisis arises. That type of toxic glutamate release, at the worst possible time, by the same cells that previously had nurtured and protected the neurons, becomes yet another major aggravating factor, which can drive a crisis condition from "terrible" to "even worse" in the aftermath of a head injury.

Accordingly, hyper-excited neurons in an injured brain can be pushed and driven into a death spiral, by a sequence of five distinct steps. Each step will lead directly to the next step, and each earlier step will then be aggravated, increased, and worsened, by the additional burdens created by the subsequent steps, in a manner that can be described as a "vicious circle" or "runaway train" condition. Those steps can be summarized as follows:

(1) in Step 1, elevated intracranial pressure will lead to a reduction in blood supply, which reduces the supply of energy and fuel that the brain needs;

(2) in Step 2, the loss of fuel and energy leads to reduction and then failure of the glutamate transport pumps, which require energy to pump free glutamate back inside the interiors of neuronal and glial cells;

(3) in Step 3, an uncontrolled increase in neuronal firing events will begin to occur, caused by excessive activation of glutamate receptors by extra-cellular glutamate, which will begin accumulating in dangerously high quantities, in the synaptic junctions between neurons, as soon as the glutamate transport system begins to fail;

(4) the initial uncontrolled surge in neuronal firing events will cause the affected neurons to begin releasing even greater quantities of glutamate and acetylcholine release, in ways which will trigger even more uncontrollable nerve-firing events, in rapidly-expanding areas of brain tissue; and, (5) every hyper-excited neuron will turn on its ion pumps, and will leave them turned on, in a desperate struggle to try to regain a "resting state" voltage. This will rapidly deplete and exhaust any remaining scarce supplies of fuel and energy, which in turn will lead to complete failure of the glutamate transport system, which will lead to even greater releases of still more glutamate and acetylcholine.

Accordingly, this sequence of steps will be fatal, unless the patient is placed in a medically-induced coma before the sequence reaches a point of causing permanent brain damage.

Fortunately, when head traumas are involved that appear to be only moderate or mild rather than severe, it usually requires at least several hours, before the growing array of contributing problems reaches a point of irreversibility.

Therefore, if diagnostic methods were available which could provide coaches, trainers, police, firemen, and the owners of places (such as ski resorts) where head traumas are likely to occur, with some method for evaluating the true severity of a head trauma, it could save lives, reduce costs, and prevent terrible suffering, including the suffering of family members and loved ones who lost (or who must spend the rest of their lives caring for) someone who was young, healthy, athletic, and promising, up until the day of an accident.

Accordingly, anyone who wishes to analyze recent patent efforts to develop better biomarkers, for analyzing and diagnosing the severity and extent of a traumatic injury to the brain, should be aware of the following items:

Issued U.S. Pat. No. 7,456,027

Published US applications 2011/056338; 2012/0322682; and 2012/0244555

Published PCT applications WO2013/086306; WO2102/151406; and WO2013/090285.

All of the above-listed items are regarded as peripheral only, and are not directly related to this invention, since none of them are believed to relate directly to "mitochondrial releasate" molecules of the type that are of direct interest herein.

Persistent Problems Caused by "Mild" TBI Events

In addition to addressing the possibility that lethal or crippling brain damage can, in some cases, be caused by what initially appeared to be a relatively mild "blow to the head", anyone who is interested in this subject should also be aware of the frequency of lingering and long-term damage at lower levels, which can be caused by concussions or similar events tat at were not life-threatening.

When someone is taken to a hospital after an apparently serious or worrisome fall, collision, or blow to the head, the standard treatment approach is to have a trained person (such as a nurse) evaluate the patient, in ways which include asking questions of him or her, so that an evaluation of the patient can be reached, using both: (i) an evaluation and ranking system called the "Glasgow Coma Score" (GCS) initially developed in Scotland, and later adopted and used at hospitals around the world); and, (ii) various types of imaging, such as computerized tomography (CT or CAT scans), magnetic resonance imaging (MRI), etc., which can detect whether bleeding is occurring, in or around the brain.

If a patient is given a "severe" ranking, immediate and strong intervention is used, including potent drugs, which in many cases can include surgery and/or a medically-induced coma. If the assessment is "moderate", lesser treatments are used, but the patient is kept in the hospital for observation, and is hooked up to continuous monitoring equipment which will sound an alarm if the patient's condition grows worse. If the assessment of the head injury is "mild", or the patient is deemed to have suffered a concussion that is not complicated or rendered more dangerous by other, additional factors, the patient usually is sent home within a few hours, with cautionary instructions to remain quiet and rest for the remainder of the day, and to make sure a caregiver is present who will keep an eye on the patient and bring him or her back to the hospital, if his/her condition gets worse rather than better.

It has been estimated that, in the U.S., at least two-thirds of TBI patients whose head injuries were sufficiently severe or worrisome to cause them to go to an hospital, are assessed as "mild" TBI or concussion patients, and are sent home within a few hours after arriving at the hospital (or after an overnight stay, if they arrive in the evening or nighttime), with no special medical treatments that required a prescription or active involvement from a doctor.

Most of those patients recover, without significant short or mid-term consequences. However, substantial numbers of such patients develop persistent neurological, behavioral, and cognitive symptoms, which often include, for example, recurring headaches, memory disturbances, difficulties in concentrating, and lingering anxiety and/or depression). These types of symptoms, if they arise following a concussion or similar head trauma, are often generally lumped together, and are referred to as "post-concussion syndrome" (PCS). It has been estimated that: (i) up to half of all concussion and mildTBI patients will have one or more symptoms that indicate persistent PCS, 3 months after the accident or concussion; and, (ii) 15% of such patients will continue to have one or more of such symptoms, a full year after the accident. Furthermore, the medical disability and insurance claims, and occupational problems (including frequent requests for time off from work) that are associated with PCS, are quite sizeable, and impose large economic burdens on society, employers, and workers.

For the foregoing reasons, it is not sufficient for people such as football coaches, policemen, or ambulance attendants to create and then rely upon a "single-moment-in-time" analysis of a head trauma, since that "snapshot" type of single-instant evaluation cannot adequately determine or foretell which players or patients are at substantially elevated risk of a serious neurologic problem that may not begin to seriously manifest and become apparent until more time has passed after a "blow to the head".

Attention must now turn to two other areas of research and technology. The first area involves a class of devices and machines that are used for computer-assisted measurements of various types of liquids and/or biomolecules. These devices and machines are widely used, both for medical diagnostics, and for biological and biochemical research, and they are discussed in the next section.

"Readable" Discs and Arrays with Affixed Reagents

For purposes of analysis and discussion, the terms "device" and "reader", as used herein, must be distinguished from each other.

The types of devices that have certain types of biological reagents affixed to them, and which will be contacted with a fluid sample that needs to be analyzed (such as a blood sample from a person who has suffered a blow to the head), are referred to herein as "readable devices", or simply as "devices". Typically, any such device will be designed for only one use, to analyze a single fluid sample. Accordingly, in the medical field, such devices are often referred to as "supplies" and/or "disposables". In patent terms, since these devices usually do not have moving parts and usually will not qualify as "machines", they are referred to as "articles of manufacture".

Because of how they are designed and used, such devices can be divided into three main functional categories. Although there is substantial overlap between these categories, those who work in this field have become accustomed to and comfortable with these terms.

(1) The first category includes spinning discs, also simply called "discs", for convenience. These are devices which are designed to rotate, while they are being "read" by a sensor machine. This class of devices is comparable to compact discs (CD's) and "digital video (or versatile) discs" (DVD's). In most cases, the types of discs that are used for medical diagnostics and biological research have the same dimensions and general design as CD's and DVD's; however, it should be noted that the reference to "CD's and DVD's" can include so-called "mini-discs", which have diameters smaller than conventional music or video discs (which are 12 cm, equal to 4.75 inches); such "mini-discs" are often used to: (i) provide the "driver" software that accompanies computer peripheral devices; and, (ii) record video files, in small portable video cameras. When mini-discs or standard-sized discs are used for medical diagnostics or biological research, one or more layers or types of fluid-handling components bioreagents are affixed to one surface of the disc. Subsequently, the spinning of the disc will generate centrifugal force, which can be used to help transport and distribute a sample of blood, urine, saliva, or other fluid across the surface of the disc, in useful ways;

(2) The second category includes "arrays", which (as used herein) covers and includes any type of non-spinning device designed for use as described herein. Stated in other words, if a single-use disposable device has biological reagents affixed to at least one surface, for use in either medical diagnostics or biological research, and if it does not spin in a rotating manner while being "read" by a sensor, then it is classified and referred to herein as an "array", rather than as a "disc".

(3) The third category, which is important because it has effectively spawned an entire biomedical and diagnostic industry, is referred to here as "microfluidic devices". These can be either spinning or non-spinning devices. Typically, these devices use fluid properties such as capillary flow, which occurs regardless of whether a disposable readable device is or is not being rotated. The factors which gather these types of devices into their own special group can be studied, at an introductory level, at the Wikipedia entry on Microfluidics, or in any of numerous syllabi which have been posted on the Internet for courses at colleges or medical schools on microfluidics. Much more detailed and extensive information is also readily available in literally hundreds of review articles on microfluidics that can be easily located by a search of the National Library of Medicine, where "microfluidics" as a search term is limited by a filter for review articles only. Two quick examples include Zhu et al 2013, entitled, "Analytical detection techniques for droplet microfluidics—a review," and Luo et al 2013, entitled, "Electrical biosensors and the label free detection of protein disease biomarkers" (where the phrase "label free detection" indicates that Luo's review specializes in bioreagents that do not use or require radioactive isotopes). Anyone who specializes in (or seriously tends to enter) this field can find still more information in any of several introduction-and-summary types of books, such as Tabeling 2010 (entitled Introduction to Microfluidics), or Nguyen et al 2006 (entitled Fundamentals And Applications of Microfluidics, Second Edition). And, for still more information on this topic, one can visit the website of an expert or company which specializes in this type of work, such as Dr. Samuel Sia's web pages that are accessed through http://orion.bme.columbia.edu/~sia/research.html, or the website of a company called Claros, which recently was ourchased by Opko Health.

The most common types of biological reagents that are affixed to these types of readable discs, arrays, or microfluidic devices, can be divided into four major categories, as follows:

1. antibodies, which will bind to specific targeted biomolecules that may be present in a liquid sample that is being tested. Because of their very high levels of selectivity and specificity, and because they can be manufactured by in vitro cell cultures without requiring live animals, monoclonal antibodies (rather than mixtures of "polyclonal" antibodies, isolated from blood serum) are usually preferred for this type of use;

2. a strand of DNA or RNA, typically having at least 10 and up to about 30 nucleotides, in single-stranded form. In most cases, the chosen sequence will be "complementary" (using the A-T and C-G binding pairs) to a known RNA sequence that is of interest. Accordingly, if copies of an RNA sequence of interest is present in a fluid sample, those molecules will bind and cling to the complementary single-stranded DNA or RNA molecules that have been affixed to a disc or array surface, at a known location;

3. molecules of a certain type of enzyme, which will catalyze a known and specific chemical reaction, if a sample of liquid that is being tested contains a particular type of "substrate" molecule;

4. "substrate" molecules that will be converted into different molecules, by an enzyme of interest, if that enzyme is present in a liquid that is being tested. These types of molecules usually are affixed to a solid support via a linker molecule or spacer chain, to make them more accessible to any enzymes in a liquid; and, 5. "hybrid"-type systems which include both nucleic acid and protein. One examples of such a hybrid system includes ChIP-on-chip devices which combine chromatin immuno-precipitation (ChIP) with microarray technology, for use with biomolecules such as transcription factors (i.e., sequence-specific DNA-binding proteins).

These types of diagnostic and analytical reagents, and the methods used to create and carry out assays using these types of reagents, are well known, and are described in numerous books and laboratory manuals that are used by biochemical researchers and lab technicians.

The electronic/computerized machines that are used to "read" the types of disc or array devices described herein are referred to herein as "readers". A typical "reader" machine suited for use as described herein will be a small and lightweight portable machine which is designed to be coupled to any of various types of portable computers. Such portable computers can include so-called "laptop" or "notebook" computers, computer "pads" or "tablets", or even "smart phones" and "personal digital assistants (PDA's) that have data display capabilities.

The coupling of a reader machine, to a laptop or other portable computer, preferably should utilize a direct ("hard-wired") connection, such as a "universal serial bus" (USB) cable. That type of coupling, via a cable that can be plugged into ports on the reader and a computer, can increase speed and reliability, and can eliminate potential problems and delays in establishing a wireless connection between two computerized devices, and it also can help preserve the confidentiality of any medical data that is being gathered or compiled on a patient. Alternately, a wireless connection (such as a "Bluetooth" or "WiFi" connection, as commonly used by cellphones, headsets, and other "peripheral" devices) can be provided and used, if desired.

In essentially all cases where spinning discs are used as the support devices for biochemical reagents, they interact with a tiny laser beam, created by a subassembly within the "reader". When discs are used to store music, video, or other types of computerized files, they are handled by reader devices that grip a disc via a hole in the center, and spin it around, while a tiny laser beam is directed against the reflective surface of the spinning disc. The laser source is mounted on a linear transport device that will move the laser beam across the reflective surface, usually starting with the innermost tracks, where the identifying directory, and other instructions and commands for such discs are located, and moving toward the outside tracks, as information on the disc is read and processed. The rotational control usually causes these types of discs to rotate faster when the laser source is near the center, and slower as the laser source moves toward the outside of the tracks; this enables the sensor and the processing system to process data at a generally stable and constant rate, which can be managed more easily, regardless of whether the laser beam is close to the center, or close to the outer rim of a disc. As the laser beam travels across the reflective surface of a CD or DVD while the disc spins, it will alternate between:

(i) being reflected back to a sensor device, in areas of the disc where the reflective surface is smooth; or, (ii) deflected, so that the beam does not return to the sensor device: (a) on surface areas where a microscopic bump is located, in discs that have been mass-manufactured; or, (b) on surfaces where a tiny patch of a photosensitive chemical has been previously burned, by a laser beam, in discs that are created one-at-a-time, using a disc drive with disc-burning capability. Accordingly, by using high-speed electronic processing systems, a laser-beam sensor inside a CD or DVD reader machine detects the pattern of 0's and 1's at any particular location on a CD or DVD, and converts that information into an electronic output signal that can be processed by an amplifier, television, or computer.

When a laser beam is used to "read" that type of disc, the beam of light never physically "touches" the disc, and will not become fouled or otherwise affected by anything affixed to the disc. Therefore, not long after the public introduction of music CD's, in the late 1970's and early 1980's, scientists realized that similar discs could be used as solid supporting surfaces that could hold and carry the types of biochemical reagents that can be used for medical diagnostics, and biochemical research. Accordingly, by the early 1980's, researchers began to test and develop compact discs, designed to be "read" by laser beams, which could be used to handle biological reagents and fluids, for medical diagnostic purposes, and for various types of biochemical research and analysis. Those types of devices have become so common and widespread that they are now commonly referred to as "Health Diagnostic Compact Discs" (abbreviated as HDCD's).

When non-spinning "arrays" (as distinct from spinning discs) are used to support the types of biomolecules that are of interest in research or medicine, a greater variety of other, additional types of sensors and detectors can be used. In some cases, an array will be held stationary, while one or more sensor devices are moved in various ways, either above or below the array; in other cases, one or more types of sensor devices can be moved into place and temporarily locked in position, above or below an array, and the array itself is then moved around. Regardless of which components are held stationary and which components are moved, any such movement usually is limited to "orthogonal" directions (i.e., right-angled directions, usually expressed in terms such as left/right, forward/backward, and up/down), since orthogonal motion is easily measured and does not require additional calculations to determine exactly where something is located, to the nearest micrometer or nanometer.

Arrays can be especially useful, and are often preferred over spinning discs, in cases where the "signal" that is generated or increased by some type of biochemical reaction is relatively weak, or requires a significant amount of time to be fully manifested or detected. For example, if a biochemical reaction involving only a very few molecules generates a small and barely detectable emission of light, phosphorescence, or radioactivity, a sensor device such as an entire plate of photodetectors, comparable to the photodetectors used to capture light and create an image in a digital camera, can be placed immediately adjacent to the array, and can be held there for as long as desired, to detect the presence and measure the strength of the weak emission. Since that type of sustained detection procedure cannot be done by a tiny laser beam that is racing at high speed across an area that stores billions of bytes of information, a stationary array is usually better suited, for detecting that type of signal, than a spinning disc.

Those who specialize in this field of art know about the capabilities and limitations of different types of discs and arrays, when used as described herein; accordingly, they can select and then optimize a suitable type of disc or array for type of biological reaction, once they know which type(s) of biomolecule(s) will be of specific interest, in any particular type of test.

Other relevant terms in this field of art include "microfluidics", "centrifugal micro-fluidic biochips", "lab on a chip," and "microarray". Anyone who wants to begin learning more about these lines of technology can begin with the Wikipedia articles under those headings, and then move beyond those introductions, into other articles, patents, and publications. For experts, numerous full-length books are available on this subject, including K. Appasani, Bioarrays: From Basics to Diagnostics (Humana Press, 2007); S. Matson, Microarray Methods and Protocols (CRC Press, 2009); W-L. Xing and J. Cheng, Biochips: Technology and Applications (Springer Publ., 2010); and B. Jordan, Microarrays in Diagnostics and Biomarker Development: Current and Future Applications (Springer Publ., 2012).

As of early 2014, as this is being written, companies that sell the types of diagnostic devices that will be used herein include Affymetrix, Illumina, GE Healthcare, Applied Biosystems, Beckman Coulter, Eppendorf Biochip Systems, Agilent, and Claros Diagnostics (now part of Opko Health). All of those companies have websites which describe the devices and machines sold by that company, and any such company will: (i) provide more information on the current devices and machines it sells, to any prospective customer; and, (ii) work with any prospective customer that is interested in developing a new assay for any specific purpose.

It should also be noted that any company which sells such devices and machines will have PhD scientists working for it, who specialize in that type of research and in those types of devices and readers. Accordingly, even though they set a relatively high standard, PhD's who specialize in this field of biochemical research establish the level of "ordinary skill", in this particular field of art. Accordingly, specialists with that level of skill are fully capable of:

(1) determining whether any particular "mitochondrial releasate" would be better suited for a "spinning disc" type of device, or a non-spinning "array" type of device; and, (2) selecting and designing an optimal analytical system and method, for detecting and quantifying even very small quantities of any such "mitochondrial releasate" in a blood sample, using the types of devices and readers that can be adapted for portable and lightweight "field use".

Mitochondria: Cell Furnaces, Apoptosis, and Death Signals

The final area of art that needs to be briefly introduced, as part of the background art, focuses on the cellular "organelles" called mitochondria.

Mitochondria are surrounded by their own membranes; they actually are the remnants of certain types of pre-bacterial cells that invaded larger cells, at a very early stage, as cellular life was developing on earth. The invading pre-bacterial cells established a symbiotic relationship with the larger "host cells" they had invaded, where: (i) the invaders began to perform a very useful role for the hosts; and, (ii) in return, the host cells provided the invaders with a sheltered and protected environment, so that the new "worker units" could concentrate on their task and perform it more effectively.

Most animal cells contain at least several dozen mitochondria, and may contain more than a hundred copies. All of them descend entirely from the maternal egg cell, with no contributions from the paternal sperm cell. Mitochondria even contain their own genetic code, which has several "codons" that are different from the corresponding "codons" that are used by genes carried within the nucleus of a cell.

Within animal cells, mitochondria perform two crucial functions. First, they are the "furnaces" (or "boiler rooms") where fuel is burned, to generate energy and power. The main type of cellular fuel is glucose, a specific type of sugar molecule. The "burning" (i.e., oxidation) process converts glucose molecules into carbon dioxide and water, in a manner that is analogous to burning wood or coal. The chemical energy stored in fuel, such as wood or coal, is converted into heat output, when the large molecules in the fuel are broken down and converted into the smaller molecules of carbon dioxide and water, which are the main chemical products that are created when carbon-containing material is oxidized (burned). The "burning" reaction that occurs inside mitochondria, which oxidize glucose and convert it into carbon dioxide and water, is called glycolysis; its energy output is "captured" in a way that can be utilized by a cell, in a reaction in which adenosine DI-phosphate (abbreviated as ADP), a low-energy substrate, is "boosted up" to a larger form called adenosine TRI-phosphate (abbreviated as ATP), a high-energy metabolite. The ATP permeates out of the mitochondria, and diffused throughout the remainder of the cell. Nearly any type of "endo-thermic" (i.e., energy-consuming) chemical reaction, inside a cell, will be able to utilize ATP, as a carrier and supply source for the energy that is needed to drive the reaction. When that happens, the energy-rich tri-phosphate molecule (ATP) drops back down to the low-energy di-phosphate version (ADP), and the ADP is then transported back to a mitochondria, so it can be used to carry out another cycle.

Accordingly, the "cell furnace" role is by far the best-known role that is performed by mitochondria. However, it is not their only role, and over the course of cellular evolution, a second crucially important role emerged, in which the mitochondria actually became the "cell executioners", which activate a hugely important process, in which aging and senescent cells are killed and digested, so that their "building blocks" can be efficiently recycled back into new, young, and viable cells.

That second role (i.e., "cell executioner") arose, during the course of early cellular evolution on this planet, because the oxidation (i.e., chemical burning) process that occurs inside mitochondria will generate some quantity of "oxygen free radicals", as byproducts of the oxidation reaction. As indicated by their names, oxygen "radicals" are aggressively unstable and highly reactive, and they will attack and damage other biomolecules in a generally random manner. One of their main modes of damage arises from a chain reaction, in which a single oxygen radical can attack and damage an unlimited number of the specialized "phospholipid" molecules that form the membranes which surround the mitochondria.

Accordingly, over a span of time that is usually measured in weeks or months, the membranes which enclose the mitochondria, inside a cell, become damaged, degraded, and "leaky". When they become degraded enough to begin leaking actively, the mitochondria begin releasing a molecule that was initially given the name "Cytochrome C", because it generated colors when viewed under a light microscope, before scientists realized that it is actually the "death messenger" molecule which activates a cell-killing process called "apoptosis".

When Cytochrome C is released by a cell, it activates a series or cascade of events which will recruit a "macrophage" cell. Macrophages are major components of the immune system; they leave the blood circulation, squeeze out through pores in the blood vessels, and slowly travel through the clear "lymph" fluid which surrounds and bathes the cells in soft tissue. Macrophages are attracted and activated by Cytochrome C, and when they reach an old and senescent cell that is releasing Cytochrome C, they will surround and effectively encapsulate and swallow the old cell, and will kill it and digest it. The macrophage will then release the "building block" molecules from the digested cell (i.e., the amino acids, nucleotides, membrane components, etc.), and those "building block" molecules will then be taken up and used by specialized cells that reproduce frequently (such cell types are often known as "blast" cells, such as fibroblasts, leukoblasts, etc.)

That cellular kill-and-recycle process is a crucial and extraordinarily useful process, in all vertebrate animals. It enables animals to continuously replace old and "senescent" cells, which gradually lose their ability to function at normal levels, with new and young cells that can start out fresh, with "peak" levels of vitality and vigor. In any muscle, ligament, tendon, or other connective tissue, and in any internal organ other than the brain or spinal cord, nearly all of the cells will last only a few months at most, before they are killed, recycled, and replaced by new cells. This is essential for creating and replenishing soft tissues that will remain firm, flexible, and vigorous for years and even decades, rather than mere weeks or months.

Accordingly, mitochondria play a central and crucial role in the cell-killing process called apoptosis.

However, that process usually requires multiple hours to play out and take effect, after a cell begins to release Cytochrome C. As a result, there has not previously been any level of substantial interest, in the types of molecules referred to herein as mitochondrial "releasates", as components that might help enable or improve rapid evaluation of athletes, soldiers, or others, within an hour or less after a "blow to the head" has stunned a person in a manner which raises the question of whether the person suffered a concussion, or is otherwise at risk of serious and possibly lasting neurologic damage.

Another reason why mitochondrial "releasates" apparently have not been of interest, for rapid evaluation of patients who have suffered a blow to the head, is that the process called "apoptosis" normally does not affect neurons, after a person has reached and passed the age of about two years old, except in unusual cases, such as cases involving certain types of neurodegenerative diseases. Because it would be impossible to replace aging neurons with newly-formed neurons in ways that could somehow duplicate the patterns of "active synapses" that enable a neuron to communicate with other neurons, higher mammals evolved in ways that somehow placed neurons in an exempt category, where they normally are not affected by the signals and molecules involved in apoptotic cell death.

And finally, a third reason why mitochondrial "releasates" apparently have not been of interest, for evaluating patients who have suffered a blow to the head, arises from the very nature of mitochondria, which are enclosed within their own separate membranes, inside a cell. The additional time delay that would be expected to occur, after a "host cell" inside the brain becomes injured due to a blow to the head, before mitochondrial "releasates" could first begin to diffuse out of injured mitochondrial membranes, and could then begin to diffuse out of the outer cell membranes and into extra-cellular lymph and/or blood, would seem to indicate that mitochondrial releasates would be "late arrivers", in a sample of blood from a patient who has suffered a serious blow to the head, compared to other molecules that would be released directly, and presumably more rapidly, from the liquid fluid (usually called "cytoplasm") that fills cells and which holds the mitochondria.

For all of those reasons, mitochondria, and the types of molecules that are released by mitochondria, have not previously received serious, substantial, and sustained attention, in various efforts to develop methods and reagents for rapid on-site diagnosis of the severity of head injuries.

Despite those issues, the Applicant herein has become convinced that mitochondrial "releasates" may well be able to provide highly useful additional information, if they are included in the types of biochemical analysis that can be performed on a small sample of blood from an injured athlete, soldier, or other person.

In particular, even if mitochondrial releasates do not show up in the very first wave (or surge) of "non-standard" metabolites that may indicate a concussion or an elevated risk of potentially lasting brain damage, they nevertheless should be evaluated seriously and carefully, as part of the effort to develop the best possible diagnostic methods, devices, and reagents, for analysing the potential severity of a head trauma.

Accordingly, one object of this invention is to establish a set of biochemical markers, which will reliably act as a predictor of the type and severity of the type of neuronal injury that is most likely to occur, during the hours following a blow to the head.

Another object of this invention is to establish a testing device and system, which will use specialized and disposable diagnostic components that have been prepared in advance and that are designed to interact with the testing device, and which can receive a small sample of blood or saliva, taken from the player, patient, or victim several minutes after the head trauma, and which will analyze a set of biochemical markers that will provide a useful predictive indicator of how severe the cellular and neuronal damage actually was, inside the brain, and which wil indicate whether a player, patient, or victim needs immediate medical attention, to prevent additional and possibly permanent brain damage.

These and other objects of the invention will become more apparent through the following summary, drawings, and detailed description.

SUMMARY OF THE INVENTION

Methods and materials are disclosed for athletic field, military, emergency-responder, or other on-site, in transit, emergency room, or similar evaluation of concussions and similar traumatic head and/or brain injuries that do not involve blood loss or skull fractures. These methods and materials involve diagnostic bioreagents (such as monoclonal antibodies, single-stranded DNA or RNA, etc.) which are affixed to surfaces of computer-readable devices (such as compact discs, readable cards or strips, etc.) that are designed to be handled by electronic sensor devices that can interact with portable computers (such as laptop computers, computer pads or tablets, smart phones, portable digital assistants, etc.). The bioreagents will be selected to detect the presence and concentration of at least two selected metabolites that will be released by mitochondria in response to severe cellular damage. Additional bioreagents may also be included, for detecting and quantifying one or more non-mitochondrial "damage-associated molecular patterns" (abbreviated as DAMP's). When used in conjunction with other available tests, which can include simple cognitive, reasoning, and/or response tests (as well as more complex analyses, if available), this type of analysis, focusing upon metabolites released by mitochondria, can help coaches, trainers, military personnel, physicians, and others, reach better and more informed and reliable assessments of the severity and proper repsonses to head traumas that otherwise can be very difficult or impossible to evaluate.

In addition, the diagnostic and analytical devices and methods disclosed herein can be expanded and enlarged, to enable additional biomolecular analyses that will indicate whether a person will tend to be more susceptible (compared to "normal" baseline levels) to long-term brain damage, or to post-concussion disorientation, depression, or similar problems, following a concussion. If someone is found to be especially susceptible to that type of damage or those types of problems, they can be advised of that fact, and can take it into account in appropriate ways, such as by choosing certain sports and/or positions to engage in, while avoiding other types of sports or activities.

BRIEF DESCRIPTION OF THE DRAWINGS

(1) 300 is a schematic depiction of a handheld diagnostic reader containing detection methodology, data handling and Bluetooth communication.

(2) 200 is a schematic depiction of a portable computer ("smart phone") capable of receiving Bluetooth communication.

(3) 100 is a schematic depiction of a data handling display visible to a user with Bluetooth communication between a portable reader and portable computer ("smart phone") and between the portable computer and central server.

(4) 40 is a schematic depiction of a removable stylet to prevent blood contamination to obtain a sample (fingerstick).

(5) 32 is a schematic depiction of a disposable diagnostic device ("module") having been contacted by a blood sample taken from a person having suffered a blow or trauma to the head wherein a first type of module has a biomolecular reagent bonded to it to identify a first mitochondrial releasate.

(6) 30 is a schematic depiction of a disposable diagnostic device ("module") having been contacted by a blood sample taken from a person having suffered a blow or trauma to the head wherein a second type of module has a biomolecular reagent bonded to it to identify a second mitochondrial releasate.

DETAILED DESCRIPTION

Figure 1:
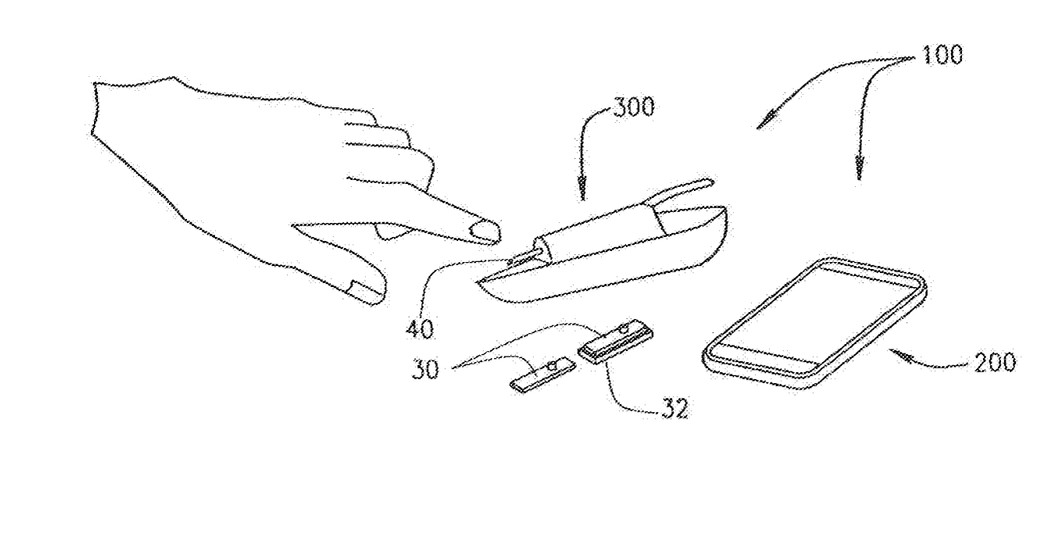
FIG. 1 is a schematic depiction of an embodiment of the hand-held diagnostic reader of the invention. The corresponding labeled parts include.

As summarized above, this invention involves materials, devices, and methods for evaluating the severity of traumatic head injuries, including concussions, which do not involve blood loss, skull fracture, or similar indicators of a major and acute crisis which requires immediate medical attention. These materials, devices, and methods are designed, in particular, for sites and situations where a relatively rapid determination must be made as to whether an athlete, soldier, accident victim, or anyone else who has been "stunned" or "shaken up", by a blow to the head, a nearby explosion, or other comparable event, can rest for a brief period, "walk it off", and then return to normal activity (such as to an ongoing athletic event, military patrol, etc.), or whether the person who suffered the blow to the head should receive prompt medical attention, to avoid or minimize lasting neurologic damage.

Accordingly, while the range and variety of uses for these types of diagnostic and evaluative materials, devices, and methods are not specifically limited to any particular class of events or activities, they should be regarded as being well-suited for use at events or in situations such as:

(1) athletic contests in which high-speed collisions between players occur, either as a normal part of the game (such as in football, hockey, etc.), or as less-frequent or incidental occurences (such as in soccer, basketball, baseball, water polo, bicycle racing, etc.);

(2) during military activities, such as training exercises or patrols where accidents, ambushes, explosions, and similar events can occur;

(3) when "first responders" (which generally includes personnel who have been trained to respond to emergencies, such as police, firemen, ambulance attendants, etc.) arrive at the site of an accident or other incident or situation involving an apparent victim of a blow to the head or comparable trauma.

These methods and materials can utilize diagnostic bioreagents that are affixed to surfaces of computer-readable devices, which are designed to be analyzed by electronic machines referred to herein as readers. As described in the Background section, and as used herein, the types of devices used for these analyses are classified as either:

(1) discs, if they spin while being "read" (usually by a laser beam); or, (2) arrays, if they do not spin while being read.

Different types of readers are used to read those various different types of devices, and as of late 2012, as this is being written, companies that sell the types of diagnostic devices that will be used herein include Affymetrix, Illumina, GE Healthcare, Applied Biosystems, Beckman Coulter, Eppendorf Biochip Systems, and Agilent. The scientists and engineers who work for those companies, on such devices and readers, are fully capable of determining the best types of devices, and bioreagents, for use in any particular test that will be designed to analyze the quantity or concentration of a "mitochondrial releasate" as described herein.

The term "mitochondrial releasate", as used herein, refers to a biomolecule which meets two criteria. First, it must be clearly known and regarded as mitochondrial, in origin. Such compounds are contained inside normal, healthy, and functioning mitochondria at concentrations which are much higher than in circulating blood, or in normal "cytoplasm" (i.e., the fluid that fills the interiors of cells, excluding fluids inside the nucleus, or inside the mitochondria. The nucleus and the mitochondria are both classified as "organelles", since they are surrounded by their own membranes, and they contain their own specialized concentrations of specific types of proteins, DNA, RNA, etc. As an arbitrary "benchmark" standard, if there is no clear consensus in the scientific and medical literature as to whether some particular type of molecule is or is not a "mitochondrial" molecule, then a "10× higher concentration" standard can be applied, as follows: if the average concentrations of some particular type of molecule, inside normal and healthy mitochondria, is at least 10-fold greater than in circulating blood or non-mitochondrial cytoplasmic fluid, then that type of molecule qualifies as mitochondrial in origin.

The form and suffix of the word "releasate" is intended to be similar to other words that relate to or involve fluid behavior, including condensates, leachates, absorbates, etc. Accordingly, to qualify as a mitochondrial releasate, a mitochondrial molecule must be released by injured, damaged, and/or dying cells, into circulating blood, in quantities that enable those particular types of molecules to be used to analyze the extent and severity of cellular or tissue damage in response to a traumatic blow or similar injury.

At the current time, as this provisional application is being written and filed, there are four specific types of candidate "mitochondrial releasates" that are believed and asserted to offer substantial utility, for evaluating the severity of a traumatic brain injury. Those four candidates can be summarized as follows:

1. First Category: mtDNA, as an Entirety

This category includes DNA sequences and segments which are specific to mitochondrial genes, as compared to nuclear genes (i.e., genes carried within the nucleus of a cell). The prefix "mt", in "mtDNA", specifically indicates that the DNA is of distinctly mitochondrial origin. Strands of mtDNA will bind, with affinity and specificity, to "complementary" DNA strands that have been affixed to the surface of a spinning disc or non-spinning array that is suited for processing and handling by the types of portable "reader" machines that are well-known and widely used for handling medical diagnostics and biochemical research. Accordingly, the types of methods and procedures that normally are used to perform "Southern blots", which are standard and well-known types of tests that are done in biochemistry labs around the world, can be used to measure the levels of mtDNA in the blood of an athlete, soldier, accident victim, or other person of interest.

To optimize the utility of these types of tests, an athlete, soldier, or other person who is at elevated risk of a collision, attack, or other form of TBI preferably should be tested, at the beginning of a season, before being deployed to a combat zone, or at a comparable suitable time, to determine both:

(i) a normal ratio between that person's mtDNA, and his/her nuclear DNA; and, (ii) the quantity of mtDNA in that person's blood, under normal conditions.

If either (i) that ratio, or (ii) the concentrations of both mtDNA and nuclear DNA, in that person's blood, is found to be significantly altered, after a blow to the head or similar event, then the altered ratio and/or increased concentrations should be treated and regarded as a warning signal that the blow to the head may have created a concussion, and should be treated as a potentially serious neurologic problem that requires prompt medical attention.

Two specific mitochondrial genes which offer good candidates for targeted analysis as described herein are:

(1) the mitochondrial gene which encodes a protein called Cytochrome B oxidase, discussed below; and, (2) the mitochondrial gene which encodes a protein called ATP synthase, subunit 6.

2. Second Category: Degraded Mitochondrial Polynucleotides

In addition to testing for unaltered mtDNA, Southern blots can also be used to test for fragments of mtDNA that have been broken into pieces. That type of breakage is accelerated, in mtDNA compared to nuclear DNA, by oxygen radicals (also referred to as oxygen free radicals, oxidative radicals, and "radical oxygen species" (ROS), which are found in abnormally high quantities inside the mitochondria (this is due to the fact that the mitochondria are the "cellular furnaces" where glucose (a sugar molecule) is "burned" (i.e., oxidized) to release its stored energy).

3. Third Category: Cytochrome C Oxidase

Cytochrome C oxidase is an enzyme which participates in the formation of "Cytochrome C", the so-called "death messenger" molecule, mentioned in the Background section. This enzyme is encoded by "nuclear genes" (i.e., genes located on the chromosomes inside the nuclei of mammalian cells). However, once formed, these enzyme molecules migrate to (or are actively transported to) the mitochondria, and are taken inside the mitochondria to a point where almost no Cytochrome C oxidase molecules remain as free molecules in the cytoplasm of a cell. Accordingly, Cytochrome C oxidase provides an example of an enzyme (protein) that is found inside mitochondria, and which does not normally otherwise exist in substantial quantities in cytoplasmic fluid, or in blood samples in healthy people.

Its presence and concentration can be detected by either:

(i) assays or procedures that use monoclonal antibodies which bind specifically to Cytochrome C oxidase; or, (ii) assays which provide a substrate that is acted upon by Cytochrome C oxidase's enzymatic activity.

4. Fourth Category: Cyclophilin D (CypD)

"Cyclophilin D" is another protein which is encoded by genes in the nuclei, but which actively migrates or is transported to mitochondria. Normally, it is affixed to mitochondrial membranes, as part of an organelle structure called the "mitochondrial permeability transition pore". As such, it normally is located near the outer surfaces of the mitochondrial membranes, and it will be released, in a relatively rapid manner, if mitochondrial membranes in a cell are seriously damaged, to a point which causes them to rupture and break apart. It can be detected by assays which use monoclonal antibodies that bind specifically to Cyclophilin D.

5. Fifth Category: ATP Synthase, Subunit 6

This protein, which is encoded by mitochondrial genes, normally is found at significant quantities, in healthy tissue, only in mitochondria, rather than in cytoplasm or blood. It can be detected by assays which use monoclonal antibodies that bind specifically to subunit 6 of the ATP synthase complex.

6. Sixth Category: High-Mobility Group Box 1 Protein (HMGB-1)

This protein, although encoded by a gene in a cell's nucleus, translocates to the mitochondria where it effects "mitochondrial quality control". Long thought to be a nuclear DNA-binding protein, it has come to prominence in the last decade because of its release from damaged and/or necrotic cells into the bloodstream, where it is a late mediator of tissue-damaging effects of sepsis and inflammation. Accordingly, it can be regarded as a prototypic "DAMP". It is a prominent pro-inflammatory mediator; and, as amphoterin, it has been shown to be essential for normal brain development. It is increased in brain and spinal cord tissue after injury, and is released into the bloodstream.

7. Seventh Category: Transcription Factor for Mitochondria A (TFAM)

This protein transcription factor, also encoded by a nuclear gene, is responsible for mitochondrial biogenesis.

TFAM is normally bound to and remains associated with mitochondrial DNA (mtDNA) when released from damaged cells. It is released from the brain after TBI. Like HMGB1, TFAM is a member of the high-mobility group (HMG) of proteins because it contains two HMG "boxes". These factors make TFAM a promising "analyte" for use as described herein.

Other Biomolecules that can Indicate Increased Susceptibility to Long-Term Problems after One or More Concussions In addition to the types of candidate molecules listed above, any of various additional types of bioreagents (such as monoclonal antibodies or strands of DNA which have specific binding affinity for any targeted biomolecules of interest in a person's blood) can be affixed to a diagnostic disc, array, or other device as described herein, which can help coaches, trainers, physicians, and others develop a better understanding of a certain person's susceptibility to neurodegenerative decay, and/or to mental or behavioral problems (such as lingering depression, disorientation, etc.), following a concussion or other head trauma.

Accordingly, if a blood test is being done on a candidate athlete, either at the start of a season or at an important milestone in his or her career (such as when a candidate athlete is applying for an athletic scholarship to college, or is attempting to be selected for a professional sports team), it would be a relatively simple and inexpensive task to use that same blood test to check for other, additional factors that may indicate a greater-than-normal susceptibility to long-term neurological, mental, or behavioral problems, if that candidate suffers a concussion.

The Applicant herein asserts that the following molecules appear to offer good and promising candidates for testing and analysis, to determine whether they can, indeed, help indicate higher-than-baseline levels of susceptibility to long-term neurological problems, following a concussion. This is not a firm assertion that these molecules do indeed play crucial and pivotal roles, which can help coaches, trainers and physicians evaluate susceptibility to long-term neurological damage following a concussion; instead, this is an assertion that at least some of these these biomolecules merit inclusion in any such diagnostic discs, arrays, and other devices, so that experts working in this field can begin gathering better and more data, to help them reach medically valid, reliable, and statistically-supported standards which will help advance the level of understanding and the state of "best practices" care and treatment, in this field of medicine.

Accordingly, the Applicant asserts and recommends that the types of diagnostic discs and arrays disclosed herein should be designed to include reagents that will provide physicians, coaches, trainers, and other analysts with data that can indicate the blood-borne concentrations of any or all of the following biomolecules:

(1) Apolipoprotein E (APO-E);

(2) TAR DNA binding protein (TDP-43; TARDBP)

(3) Angiotensin-converting enzyme (ACE); "serpin" proteins, such as protease nexin 1 (PN1; SERPINE1); neuroserpin (SERPINI1); and, plasminogen activator inhibitor 1 (PAI-1; Serpine1 or SERPINE1)

(4) cytokine genes and inflammatory mediators, and/or protein subunits from their receptors; examples include Interleukin-1 beta (abbreviated as IL-1β or IL-1B), and tumor necrosis factor alpha (abbreviated as TNF-α, TNF-A, or simply TNF);

(5) Thrombomodulin (THBD), and endothelial cell protein C receptor (EPCR; PROCR);

(6) 5-hydroxytryptamine (serotonin) receptor 2A (5-HT2A; HTR2A) and solute carrier family 6 (neurotransmitter transporter, 5-HT) and/or member 4 (SLC6A4; or SERT);

(7) Certain types of "high mobility group" proteins, including "HMG box 1 protein" (HMGB1); and, (8) certain proteins referred to as "RAGE" proteins (which refers to "receptor for advanced glycation endproducts", also given the acronym AGER).

Thus, there has been shown and described a new and useful set of diagnostic devices and methods which can help coaches, trainers, first-responders, military personnel, physicians, and other, in their efforts to evaluate the severity of damage that may have been caused by a concussion or other head trauma. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Zhu Y, Fang Q, "Analytical detection techniques for droplet microfluidics—a review," Anal Chim Acta. 2013 Jul. 17; 787:24-35

Luo X, Davis J J., "Electrical biosensors and the label free detection of protein disease biomarkers", Chem Soc Rev. 2013 Jul. 7; 42(13):5944-62

Tabeling, P., Introduction to Microfluidics, Oxford Univ. Press (2010)

Nam-Trung Nguyen and Steven T. Wereley, Fundamentals And Applications of Microfluidics, Second Edition, 2006, Integrated Microsystems

The invention claimed is:

1. A diagnostic reader, comprising a portable unit designed to be carried by hand and coupled to a portable computer to allow data transfer between said diagnostic reader and said portable computer, wherein said diagnostic reader is designed to handle a disposable diagnostic device which has been contacted by a blood sample taken from a person who may have suffered a blow or trauma involving the person's head, and wherein said disposable diagnostic device has:
   a. at least one first reactive surface which has a first type of biomolecular reagent bonded to it which will enable a trained user to measure a blood-borne concentration of at least one first mitochondrial releasate; and,
   b. at least one second reactive surface which has a second type of biomolecular reagent bonded to it which will enable a trained user to measure a blood-borne concentration of at least one second mitochondrial releasate; and,
   and wherein said diagnostic reader has data handling means selected from the group consisting of:
   i. displaying, in a manner visible to a user, both of the blood-borne concentrations of said first and second mitochondrial releasates; and,
   ii. transferring, to a portable computer which has a display monitor, both of the blood-borne concentrations of said first and second mitochondrial releasates.

2. The diagnostic reader of claim 1 wherein said first and second mitochondrial releasates are selected from the group consisting of:

(1) DNA segments which are specific to mitochondrial genes and which do not normally occur in human nuclear DNA;

(2) fragments of DNA that have been degraded by oxidative radicals in ways that normally are found, in humans, only in DNA fragments that have been released by mitochondria;

(3) Cytochrome C oxidase;

(4) Cyclophilin D;

(5) subunit 6 of ATP synthase;

(6) high-mobility group box 1 protein (HMGB-1);

(7) transcription factor for Mitochondria A.

3. The diagnostic reader of claim 1 wherein both of said first and second reactive surfaces are positioned in different locations on a single disposable diagnostic device.

4. The diagnostic reader of claim 1 wherein said diagnostic reader is also capable of reading data from said disposable diagnostic device which have distinct areas that have been coated with biomolecular reagents that will indicate concentrations of one or more blood-borne human proteins selected from the group consisting of:

(1) apolipoprotein E;

(2) apolipoprotein A-1;

(3) one or more selected TAR DNA binding proteins;

(4) one or more cellular damage-related proteins selected from the group consisting of angiotensin-converting enzyme serpin proteins, and plasminogen activator inhibitors;

(5) cytokines or inflammatory mediators;

(6) mRNA from genes which encode subunits of receptors which interact with cytokines or inflammatory mediators;

(7) thrombomodulin (THBD);

(8) endothelial cell protein C receptor;

(9) 5-hydroxytryptamine receptor 2A;

(10) solute carrier family 6 (neurotransmitter transporter, 5-HT);

(11) the human protein designated as SLC6A4;

(12) "high mobility group" proteins; and, (13) proteins normally found in receptors for advanced glycation endproducts".

* * * * *